US007959958B2

(12) United States Patent
Furrer et al.

(10) Patent No.: US 7,959,958 B2
(45) Date of Patent: Jun. 14, 2011

(54) COOLING COMPOUNDS

(75) Inventors: Stefan Michael Furrer, Cincinnati, OH (US); Gregory Lee Yep, Cincinnati, OH (US); Eric Flamme, Cincinnati, OH (US)

(73) Assignee: Givaudan, S.A., Vernier (CH)

( * ) Notice: Subject to any disclaimer, the term of this patent is extended or adjusted under 35 U.S.C. 154(b) by 171 days.

(21) Appl. No.: 12/137,928

(22) Filed: Jun. 12, 2008

(65) Prior Publication Data

US 2008/0311232 A1   Dec. 18, 2008

Related U.S. Application Data

(60) Provisional application No. 60/934,382, filed on Jun. 13, 2007.

(51) Int. Cl.
*A61K 36/534* (2006.01)
*A61K 31/195* (2006.01)
*A61K 31/19* (2006.01)

(52) U.S. Cl. .................... 424/747; 514/561; 514/569

(58) Field of Classification Search .................. None
See application file for complete search history.

(56) References Cited

U.S. PATENT DOCUMENTS

| | | | |
|---|---|---|---|
| 3,516,943 A | 6/1970 | Brynko et al. |
| 4,150,052 A | 4/1979 | Watson et al. |
| 4,285,984 A | 8/1981 | Huber |
| 4,351,347 A | * | 9/1982 | Sprecker .................. 131/276 |
| 5,759,599 A | 6/1998 | Wampler et al. |
| 6,039,901 A | 3/2000 | Soper et al. |
| 6,045,835 A | 4/2000 | Soper et al. |
| 6,056,949 A | 5/2000 | Menzi et al. |
| 6,106,875 A | 8/2000 | Soper et al. |
| 6,123,974 A | 9/2000 | Gautschi et al. |
| 6,222,062 B1 | 4/2001 | Anderson et al. |
| 6,306,818 B1 | 10/2001 | Anderson et al. |
| 6,325,859 B1 | 12/2001 | De Roos et al. |
| 6,325,951 B1 | 12/2001 | Soper et al. |
| 6,335,047 B1 | 1/2002 | Daniher et al. |
| 6,348,618 B1 | 2/2002 | Anderson et al. |
| 6,387,431 B1 | 5/2002 | Gautschi |
| 6,426,108 B1 | 7/2002 | Gautschi |
| 6,436,461 B1 | 8/2002 | Bouwmeesters et al. |
| 6,440,912 B2 | 8/2002 | McGee et al. |
| 6,451,366 B1 | 9/2002 | Daniher et al. |
| 6,482,433 B1 | 11/2002 | De Roos et al. |
| 6,610,346 B1 | 8/2003 | Acuna et al. |
| 6,689,740 B1 | 2/2004 | McGee et al. |
| 6,805,893 B2 | 10/2004 | Acuna et al. |
| 6,869,923 B1 | 3/2005 | Cunningham et al. |
| 2001/0008635 A1 | 7/2001 | Quellet et al. |
| 2002/0081370 A1 | 6/2002 | Daniher et al. |
| 2003/0082272 A1 | 5/2003 | Bouwmeesters et al. |
| 2003/0165587 A1 | 9/2003 | Binggeli et al. |
| 2004/0047960 A1 | 3/2004 | Acuna et al. |
| 2005/0207993 A1 | 9/2005 | Bazemore et al. |
| 2005/0214337 A1 | 9/2005 | McGee et al. |
| 2005/0227906 A1 | 10/2005 | Schudel et al. |
| 2005/0233042 A1 | 10/2005 | Galopin et al. |
| 2006/0035008 A1 | 2/2006 | Virgallito et al. |
| 2006/0154850 A1 | 7/2006 | Quellet et al. |
| 2006/0172917 A1 | 8/2006 | Vedantam et al. |
| 2006/0276667 A1 | 12/2006 | Galopin et al. |
| 2008/0319055 A1 | 12/2008 | Cole et al. |

FOREIGN PATENT DOCUMENTS

| | | |
|---|---|---|
| EP | 0 199 257 A2 | 10/1986 |
| GB | 1351761 | 5/1974 |
| GB | 1351762 | 5/1974 |
| GB | 1 502 680 | 3/1978 |
| JP | 05308995 | * 11/1993 |
| WO | WO 01/03825 A1 | 1/2001 |
| WO | WO 2004/034791 A1 | 4/2004 |
| WO | WO 2005/049553 A1 | 6/2005 |
| WO | WO 2006/056096 A1 | 6/2006 |
| WO | WO 2006/099762 A1 | 9/2006 |
| WO | WO 2007/019719 A1 | 2/2007 |

OTHER PUBLICATIONS

STN Report (Accession No. 1994:481123).*
Derwent Report (Accession No. 1994-002182).*
www.thegoodscentscompany.com (available online as of Jun. 5, 2006 as evidenced by the attached Internet Archive Report).*
Williams et al (Foye's Principles of Medicinal Chemistry, 5th Edition, pp. 59-61, 2002).*
Mamedov et al (Russian J Organic Chem 42:1137-1140, 2006).*
Tomaru, Junichiro, et al., "Manufacture of (−)-(1S,2S,4R)-exo-2-norbornanol with lipase", Chemical Abstracts Service, Databse CA, Aug. 20, 1994, Accession No. 1994:481123, XP002566393.
PCT/CH2008/000266—International Search Report. Feb. 15, 2010.

* cited by examiner

*Primary Examiner* — Brandon J Fetterolf
*Assistant Examiner* — Craig Ricci
(74) *Attorney, Agent, or Firm* — Curatolo Sidoti Co., LPA; Joseph G. Curatolo; Salvatore A. Sidoti

(57) ABSTRACT

A cooling composition comprising at least one compound of the Formula I

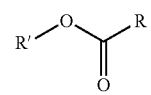

in which R is selected from the group of moieties consisting of
$(CH_2)_n COOR''$;
$(CH_2)_n CONMe_2$;
$(CH_2)_n OR''$; and
$CHNH_2CH_3$;
where n is 1-3 and R" is independently selected from hydrogen, methyl and ethyl; and
R' is selected from the group consisting of the moieties fenchyl, D-bornyl, L-bornyl, exo-norbornyl, 2-methylisobornyl, 2-ethylfenchyl, 2-methylbornyl, cis-pinan-2-yl, verbanyl and isobornyl.
The compositions are useful in providing cooling sensations to the skin or mucous membranes of the body.

7 Claims, No Drawings

COOLING COMPOUNDS

This application claims the benefits of the filing date of U.S. Provisional Application for Patent Ser. No. 60/934,382, filed Jun. 13, 2007, incorporated herein be reference.

This disclosure relates to cooling compositions.

Cooling compounds, that is, chemical compounds that impart a cooling sensation to the skin or the mucous membranes of the body, are well known to the art and are widely used in a variety of products such as foodstuffs, tobacco products, beverages, dentifrices, mouthwashes and toiletries.

One class of cooling compounds that has enjoyed substantial success consists of N-substituted p-menthane carboxamides. Examples of these compounds are described in, for example, British Patents GB 1,351,761, GB 1,351,762 and U.S. Pat. No. 4,150,052, and International publications WO 2005/049553 and WO 2007/019719.

It has now been found that an entirely different group of compounds exhibits a cooling effect that is both surprisingly strong and long-lasting. There is therefore provided a cooling composition comprising a composition base and at least one compound of the formula I

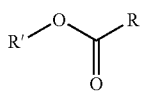
I in which R is selected from the group of moieties consisting of
$(CH_2)_n COOR''$;
$(CH_2)_n CONMe_2$;
$(CH_2)_n OR''$; and
$CHNH_2CH_3$;
where n is 1-3 and R'' is selected from hydrogen, methyl and ethyl; and R' is selected from the group consisting of the moieties fenchyl, D-bornyl, L-bornyl, exo-norbornyl, 2-methylisobornyl, adamantyl, 2-ethylfenchyl, 2-methylbornyl, cis-pinan-2-yl, verbanyl and isobornyl.

There is additionally provided a method of providing a cooling sensation to the skin or the mucous membranes of the body, comprising the application thereto of a composition comprising a composition base and at least one compound of the Formula I, as hereinabove defined.

In particular embodiments, R is selected from
$(CH_2)_2 COOR''$, where R'' is selected from hydrogen, methyl and ethyl;
$(CH_2)_2 CONMe_2$;
$(CH_2)_2 OR''$; where R'' is selected from hydrogen and methyl; and
$CHNH_2CH_3$. ("Me" indicates a methyl group.)

R' is selected from the moieties

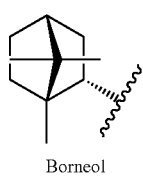
Borneol

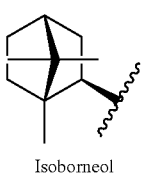
Isoborneol

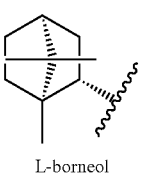
L-borneol

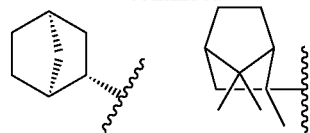

exo-Norborneol    2-Methylisoborneo

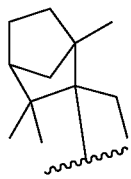   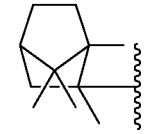   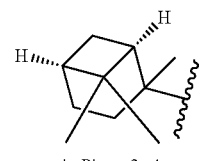

2-Ethylfenchol    2-Methylborneol    cis-Pinan-2-ol

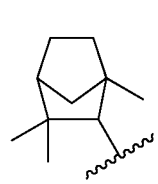   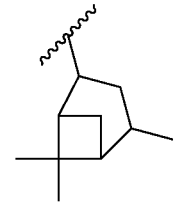   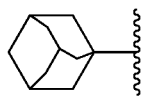

fenchol    verbanol    Adamantanol particular examples of R' being D- & L-borneol, isoborneol, fenchol and verbanol.

In one particular embodiment, R has the formula

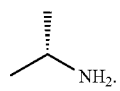

Specific examples of compounds of Formula I are:
4-oxo-4-(1S,2R,4S) 1,7,7-trimethylbicyclo[2.2.1]heptan-2-yloxybutanoic acid;
4-oxo-4-((1R,2S,4R)-1,7,7-trimethylbicyclo[2.2.1]heptan-2-yloxy)butanoic acid;
4-((1S,2S,4R)-bicyclo[2.2.1]heptan-2-yloxy-4-oxobutanoic acid;
4-oxo-4-((1R,2R,4R)-1,7,7-trimethylbicyclo[2.2.1]heptan-2-yloxy)butanoic acid;
4-oxo-4-(4,6,6-trimethylbicyclo[3.1.1]heptan-2-yloxy)butanoic acid;
Ethyl (2R)-1,3,3-trimethylbicyclo[2.2.1]heptan-2-yl malonate;
(2R)-1,3,3-trimethylbicyclo[2.2.1]heptan-2-yl 4-(dimethylamino)-4-oxobutanoate;
D-alanine fenchyl ester; and
4-oxo-4-((1R,2R,4S)-1,3,3-trimethylbicyclo[2.2.1]heptan-2-yloxy)butanoic acid.

Some of these compounds are novel. There is therefore also provided the chemical compounds ethyl (2R)-1,3,3-trimethylbicyclo[2.2.1]heptan-2-yl malonate, (2R)-1,3,3-trimethylbicyclo[2.2.1]heptan-2-yl 4-(dimethylamino)-4-oxobutanoate and 4-oxo-4-(4,6,6-trimethylbicyclo[3.1.1]heptan-2-yloxy)butanoic acid.

The compounds of formula I may comprise one or more chiral centres and as such may exist as a mixture of stereoisomers, or they may be resolved as isomerically pure forms. Resolving stereoisomers adds to the complexity of manufacture and purification of these compounds and so it is preferred to use the compounds as mixtures of their stereoisomers simply for economic reasons. However, if it is desired to prepare individual, stereoisomers, this may be achieved according to methods known in the art, e.g. preparative HPLC and GC or by stereoselective syntheses.

The compounds may be easily prepared and isolated by art-recognized methods.

They are distinguished from similar compounds of the prior art by their surprisingly high cooling effect (up to 100 times higher than that of similar known compounds) and by the longevity of the cooling effect. These compounds also have a high solubility in oily solvents, such as mint oils. These features expand the uses of cooling compounds to a larger variety of products.

The compounds may be used in compositions that are applied to the mouth or the skin to give a cooling sensation. The compositions comprise the compound (more than one such compound may be used), plus a composition base, by which term is meant all the other art-recognised ingredients necessary to make a composition that is suitable for application or ingestion. Such a composition base can range from a single substance, such as a solvent, to a full product formulation for, for example, a foodstuff, beverage, confectionery item, cream, salve, spray, dentifrice, medicine or ointment. Other examples of compositions thus prepared will appear hereinunder.

By "applying" is meant any form of bringing into contact, for example, oral ingestion or, in the case of tobacco products, inhalation. In the case of application to the skin, it may be, for example, by including the compound in a cream or salve, or in a sprayable composition. There is also provided, therefore, a method of providing a cooling effect to the mouth or skin by applying thereto a composition or a product comprising a compound as hereinabove described.

The range of products in which the compounds may be used is very wide, and it includes by way of example only, dentifrices such as toothpaste and toothgel mouthwashes, foodstuffs, beverages, confectionery, tobacco products, skin creams and ointments, both cosmetic and medicinal.

Products that are applied to the oral mucosa may include foodstuffs and beverages taken into the month and swallowed, and products taken for reasons other than their nutritional value, e.g. tablets, mouthwash, throat sprays, dentifrices and chewing gums. Products that are applied to the skin may be selected from perfumes, toiletries, lotions, oils and ointments, applicable to the skin of the human body, whether for medical or other reasons.

Accordingly, in a further aspect, there is provided a composition comprising an amount of at least one compound of formula (I) sufficient to stimulate the cold receptors in the areas of the skin or mucous membrane with which the composition comes into contact and thereby promote the desired cooling effect. A cooling effect may be achieved upon application of a product, for example, mouthwash or chewing gums, to the mucous membrane, e.g. oral mucosa, comprising less than 2000 ppm, in certain embodiments between 10 and 500 ppm, such as about 50 ppm, of a compound of formula (I). If used for beverages the addition of about 1 to 10 ppm may be sufficient to achieve a cooling effect.

Particular examples of foodstuffs and beverages may include, but are not limited to, beverages, alcoholic or non-alcoholic, such as fruit juice beverages, fruit liquors, milk drinks, carbonated beverages, refreshing beverages, and health and nutrient drinks; frozen confectionery such as ice creams and sorbets; desserts such as jelly and pudding; confectionery such as cakes, cookies, chocolates, and chewing gum; jams; candies; breads; tea beverages such as green tea, black tea, chamomile tea, mulberry leaf tea, Roobos tea, peppermint tea; soaps; seasonings; instant beverages; snack foods and the like.

Further examples of topical products may include, but are not limited to, skin-care cosmetics, such as cleansing tissues, talcum powders, face creams, lotions, tonics and gels, hand creams, hand- and body lotions, anticellulite/slimming creams and—lotions, lotions, balms, gels, sprays and creams; sunburn cosmetics including sunscreen lotions, balms, gels, sprays and creams; after sun lotions, sprays and creams; soaps, toothpicks, lip sticks, agents for bathing, deodorants and antiperspirants, face washing creams, massage creams, and the like.

Thus there is further provided a consumer product selected from at least one of products that, are applied to the mucous membrane, products that are applied to the oral mucosa, and products that are applied to the skim such as topical products, oral care products, nasal care products, toilet articles, ingestible products and chewing gum, and the like, the end-product comprises a composition base or a product base and an effective amount of at least one cooling compound of formula (I) as hereinabove defined.

The compounds as hereinabove described, may be used alone or in combination with other cooling compounds known in the art e.g. menthol, menthone, isopulegol, N-ethyl p-menthanecarboxamide (WS-3), N,2,3-trimethyl-2-isopropylbutanamide (WS-23), ethyl N-[[5-methyl-2-(isopropyl) cyclohexyl]carbonyl]glycinate, menthyl lactate, menthone glycerine acetal (Frescolat® MGA), mono-menthyl succinate (Physcool®), mono-menthyl glutarate, O-menthyl glycerine (CoolAct® 10) and 2-sec-butylcyclohexanone (Freskomenthe®), menthane, camphor, pulegol, cineol, mint oil, peppermint oil, spearmint oil, eucalyptus oil, 3-1-menthoxypropane-1,2-diol, 3-1-menthoxy-2-methylpropane-1,2-diol, p-menthane-3,8-diol, 2-1-menthoxyethane-1-ol, 3-1-menthoxypropane-1-ol, and 4-1-menthoxybutane-1-ol.

Other examples include the compounds described in the abovementioned British Patents GB 1,351,761, GB 1,351, 762, U.S. Pat. No. 4,150,052 and International publications WO 2005/049553 and WO 2007/019719, all of which, are incorporated herein by reference.

The cooling compounds may be employed into the products simply by directly mixing the compound with the product, or they may, in an earlier step, be entrapped with an entrapment material such as polymers, capsules, microcapsules or nanocapsules, liposomes, film formers, absorbents such as cyclic oligosaccharides, or they may be chemically bonded to a substrate, which are adapted to release the cooling compound upon application of an external stimulus such as temperature, enzyme or the like, and then mixed with the product. Or they may be added while being solubilized, dispersed, or diluted, using alcohols or polyhydric alcohols, such as, glycerine, propylene glycole, triazethine and mygliol, natural gums such as gum Arabic, or surfactants, such as glycerine fatty acid esters and saccharide fatty acid esters.

The compositions will now be further described, with reference to the following non-limiting examples.

EXAMPLE 1

4-oxo-4-(1S,2R,4S)1,7,7-trimethylbicyclo[2.2.1] heptan-2-yloxybutanoic acid a) Succinic acid monophenethyl ester In a 500 mL round bottom flask, fitted with a reflux, condenser, succinic anhydride (10.03 g, 1.2 eq.) and dimethylaminopyridine (10.2 g, 1 eq.) and benzyl alcohol (9.01 g, 1 eq.) in MTBE (250 mL) were combined. The reaction mixture was placed under inert atmosphere and stirred in an oil bath at 68° C. for 4 hours. The reaction was then quenched with a solution of 10% NaHCO$_3$ and extracted with MTBE. The organic layer was washed with NaHCO$_3$ and brine. The organic layer was collected, dried using MgSO$_4$, and concentrated to give a white solid. The crude product was purified using column chromatography to give 14.1 g of white crystals.

m.p. 60-62° C.

$^1$H NMR (CDCl$_3$) δ: 7.4-7.3 (m, 5H), 5.17 (s, 2H), 2.75-2.65 (m, 4H).

$^{13}$C NMR (CDCl$_3$) δ: 178.4, 171.92, 135.71, 128.57, 128.29, 128.20, 66.65, 28.92, 28.79.

GC-MS (E1): 208 (M$^+$), 190, 180, 162, 108, 107, 101, 91, 79, 65, 56, 45, 29.

b) Benzyl (1S,2R,4S) 1,7,7-trimethylbicyclo[2.2.1]heptan-2-yl succinate

In a 300 mL round bottom flask, fitted with reflux condenser, 4-(benzyloxy)-4-oxobutanoic acid (1.80 g, 1 eq., of Example 1) and anhydrous tetrahydrofuran (85 mL) were added. The reaction mixture was stirred under inert atmosphere and L-borneol (1.34 g, 1 eq.) was added, followed by the addition of HOBT (1.28 g, 1.1 eq.), EDC-HCl (1.81 g, 1.1 eq.) and DMAP (1.12 g, 1.1 eq). The reaction was heated in an oil bath at 50° C. for several hours until monitoring showed a substantial amount of product formation. The reaction mixture was filtered, concentrated and extracted with MTBE versus 1N HCl. The organic layer was washed with 1N HCl and brine, dried over MgSO$_4$ and concentrated. The crude product was purified using column chromatography to give 1.83 g of a colorless oil (62%).

$^1$H NMR (CDCl$_3$) δ: 7.4-7.27 (m, 5H), 5.11 (s, 2H), 4.92-4.85 (m, 1H), 2.72-2.61 (m, 4H), 2.4-2.29 (m, 1H), 1.99-1.82 (m, 1H), 1.8-1.65 (m, 2H), 1.35-1.15 (m, 2H), 1.0-0.91 (d, 1H), 0.9-0.85 (d, 6H), 0.8 (s, 3H).

$^{13}$C NMR (CDCl$_3$) δ: 199.1, 198.5, 173.37, 135.78, 128.57, 128.25, 80.33, 66.55, 48.78, 47.81, 44.87, 36.66, 29.50, 29.33, 28.00, 27.09, 19.69, 18.83, 13.46.

GC-MS: 344 (M$^+$), 208, 153, 137, 121, 109, 91, 92, 94, 81, 69, 55, 41, 29.

c) 4-oxo-4-(1S,2R,4S) 1,7,7-trimethylbicyclo[2.2.1]heptan-2-yloxybutanoic acid

Benzyl (1S,2R,4) 1,7,7-trimethylbicyclo[2.2.1]heptan-2-yl succinate (1.59 g, 1 eq, of Example 3) was placed in a 300 mL round bottom flask with THF (130 mL). 10% Pd/C (0.159 g, 10% by weight of starting material) was added and the reaction mixture was stirred. The flask was evacuated and then filled with nitrogen 3 times. Finally the flask was evacuated and hydrogen was introduced. The reaction was stirred on high for 16 hours at room temperature and then filtered over a celite/sand plug. The filtrate was concentrated and purified by column chromatography to give 1.02 g of a white powder (87%).

m.p. 61-63.2° C.

$^1$H NMR (CDCl$_3$) δ: 11.4-11.1 (s, 1H), 5.0-4.8 (d, 1H), 2.73-2.5 (m, 4H), 2.4-2.21 (m, 1H), 1.99-1.83 (m, 1H), 1.8-1.6 (m, 2H), 1.4-1.15 (m, 2H), 1.0-0.9 (m, 1H), 0.88-0.8 (d, 6H), 0.79-0.7 (s, 3H).

$^{13}$C NMR (CDCl$_3$) δ: 178.1, 172.34, 80.50, 48.78, 47.79, 44.85, 36.59, 29.27, 29.14, 27.98, 27.07, 19.67, 18.80, 13.40.

GC-MS: 254 (M$^+$), 154, 136, 121, 108, 101, 95, 93, 80, 69, 67, 55, 41, 29.

EXAMPLE 2

4-oxo-4-((1R,2S,4R)-1,7,7-trimethylbicyclo[2.2.1]heptan-2-yloxy)butanoic acid

The procedure outlined in Example 1 was repeated with borneol resulting in 4-oxo-4-((1R,2S,4R)-1,7,7-trimethylbicyclo[2.2.1]heptan-2-yloxy)butanoic acid.

$^1$H NMR (CDCl$_3$) δ: 5.0-4.85 (d, 1H), 2.75-2.59 (m, 4H), 2.4-2.28 (m, 1H), 2.0-1.85 (m, 1H), 1.8-1.65 (m, 2H), 1.38-1.25 (m, 2H), 1.05-0.95 (m, 1H), 0.90-0.82 (d, 6H), 0.82-0.79 (s, 3H).

$^{13}$C NMR (CDCl$_3$) δ: 178, 172, 80.49, 48, 44.88, 36.62, 29.30, 29.09, 27.98, 27.08, 26.83, 19.07, 13.39.

GC-MS: 254 (M$^+$), 154, 136, 121, 108, 101, 95, 93, 81, 80, 69, 67, 55, 41, 29.

EXAMPLE 3

4-((1S,2S,4R)-bicyclo[2.2.1]heptan-2-yloxy)-4-oxobutanoic acid

The procedure outlined in Example 1 was repeated with exo-norborneol resulting in 4-((1S,2S,4R)-bicyclo[2.2.1]heptan-2-yloxy)-4-oxobutanoic acid.

$^1$H NMR (CDCl$_3$) δ: 10.5 (s, 1H), 4.7-4.6 (d, 1H), 2.7-2.6 (d, 2H), 2.6-2.5 (d, 2H), 2.32-2.2 (s, 2H), 1.79-1.65 (m, 1H), 1.6-1.35 (m, 4H), 1.2-1.0 (m, 3H).

$^{13}$C NMR (CDCl$_3$) δ: 192, 171.69, 78.13, 41.39, 39.47, 35.36, 35.23, 29.28, 28.99, 28.10, 24.23.

GC-MS: 206, 119, 112, 111, 101, 95, 94, 79, 73, 67, 66, 55, 45, 41, 39, 29.

EXAMPLE 4

4-oxo-4-((1R,2R,4R)-1,7,7-trimethylbicyclo[2.2.1]heptan-2-yloxy)butanoic acid

The procedure outlined in Example 1 was repeated with isoborneol resulting in 4-oxo-4-((1R,2R,4R)-1,7,7-trimethylbicyclo[2.2.1]heptan-2-yloxy)butanoic acid.

$^1$H NMR (CDCl$_3$) δ: 10.5 (s, 1H), 4.75-4.62 (m, 1H), 2.7-2.51 (m, 4H), 1.85-1.49 (m, 5H), 1.17-1.01 (m, 2H), 0.98 (s, 3H), 0.81 (s, 6H).

$^{13}$C NMR (CDCl$_3$) δ: 177.83, 171.48, 81.61, 48.70, 46.89, 45.03, 38.70, 33.74, 29.30, 28.99, 27.00, 20.07, 19.81, 11.32.

GM-MS: 254 (M$^+$), 154, 136, 121, 110, 108, 107, 101, 95, 93, 91, 79, 67, 55, 41, 29.

EXAMPLE 5

4-4-(4,6,6-trimethylbicyclo[3.1.1]heptan-2-yloxy)butanoic acid a) Benzyl-4-chloro-4-oxobutanoate 4-(benzyloxy)-4-oxobutanoic acid (6.16 g, 1 eq, from Example 1a) was dissolved in toluene (20 mL) and placed in a 300 mL round bottom flask, fitted with a condenser. While the reaction was stirred under inert atmosphere, thionyl chloride (5.30 g, 1.5 eq) was added. A few drops of DMF were also added and tire reaction mixture was heated to 35° C. for 45 minutes and then to 60° C. for 2 hours. The solution was concentrated to 6.71 g of brownish oil.

b) Benzyl 4,6,6-trimethylbicyclo[3.1.1]heptan-2-yl succinate

Benzyl-4-chloro-4-oxobutanoate (3.22 g, 1 eq, from Example 2) was dissolved in MTBE (100 mL) in a 300 mL round bottom flask. Verbanol™ (2.12 g, 1 eq) and triethylamine (1.39 g, 1 eq) were added and the reaction was heated at 40° C. and stirred overnight. The reaction mixture was extracted with a dual-layer MTBE-1N HCl system. The organic layer was washed with brine, dried over MgSO$_4$ and concentrated. Toe crude product was purified using column chromatography to give 3.45 g of a clear oil (73%).

$^1$H NMR (CDCl$_3$) δ: 7.4-7.28 (m, 5H), 5.23-5.15 (m, 1H), 5.12 (s, 2H), 2.7-2.5 (m, 6H), 2.4-2.3 (m, 1H), 2.1-2.0 (m, 2H), 1.85-1.79 (m, 1H), 1.5-1.4 (m, 1H), 1.21 (s, 3H), 1.12 (s, 3H), 1.01-1.09 (d, 3H).

$^{13}$C NMR (CDCl$_3$) δ: 172.12, 171.65, 135.83, 128.55, 128.23, 128.19, 76.00, 66.49, 47.77, 45.80, 45.06, 37.96, 34.39, 32.78, 31.57, 31.27, 29.66, 29.29, 28.62, 24.11, 22.63, 21.76, 14.08.

GC-MS: 344 (M$^+$), 209, 153, 136, 121, 107, 91, 81, 69, 55, 41, 29.

c) 4-oxo-4-(4,6,6-trimethylbicyclo[3.1.1]heptan-2-yloxy)butanoic acid

The procedure outlined in Example 1c is repeated with Benzyl 4,6,6-trimethylbicyclo[3.1.1]heptan-2-yl succinate (example 2b), resulting in 4-oxo-4-(4,6,6-trimethylbicyclo[3.1.1]heptan-2-yloxy)butanoic acid.

1H NMR (CDCl3): 5.22-5.17 (m, 1H), 2.27-2.55 (m, 4H), 2.4-2.31 (m, 1H), 2.11-2.0 (m, 2H). 1.85-1.79 (m, 1H), 1.52-1.43 (m, 1H), 1.28 (s, 1H), 1.22 (s, 3H), 1.1 (s, 3H), 1.09-1.03 (d, 3H), 0.8-0.74 (d, 1H).

13C NMR (CDCl3): 177.83, 171.59, 76.18, 47.74, 45.77, 37.95, 34.39, 31.25, 29.41, 29.01, 28.59, 26.94, 24.06, 21.74.

GC-MS: 239 (M-CH3) 199, 154, 139, 136, 121, 108, 107, 105, 101, 93, 85, 81, 80, 79, 77, 69, 67, 55, 43, 41, 39, 29.

EXAMPLE 6

Ethyl (2R)-1,3,3-trimethylbicyclo[2.2.1]heptan-2-yl malonate

R-fenchol (2.87 g 1 eq), monoethyl malonate (2.57 g, 1 eq) and methylene chloride (85 mL) were added to a round bottom flask. After cooling the reaction to 0° C., DCC (3.87 g, 1 eq) and DMAP (0.23 g, 0.1 eq) along with methylene chloride (35 mL) were added. The reaction was stirred overnight at room temperature. The reaction mixture was extracted with a dual-layer MTBE—brine system. The organic layer was dried over MgSO$_4$, concentrated and purified by column chromatography, to give 3.58 g of a clear liquid (72%).

$^1$H NMR (CDCl$_3$) δ: 4.4 (d, 1H), 4.3-4.1 (m, 2H), 3.4 (s, 2H), 1.75-1.6 (m, 3H), 1.6-1.55 (d, 1H), 1.52-1.4 (m, 2H), 1.35-1.25 (t, 3H), 1.2-1.15 (d, 1H), 1.1 (s, 3H), 1.05 (s, 3H), 0.7 (s, 3H).

$^{13}$C NMR (CDCl$_3$) δ: 166.92, 166.60, 87.45, 61.44, 48.37, 48.28, 41.84, 41.31, 39.48, 29.66, 26.48, 25.75, 20.08, 19.27, 14.08.

GC-MS: 268 (M$^+$), 153, 136, 121, 115, 107, 93, 81, 80, 69, 55, 43, 29.

EXAMPLE 7

(2R)-1,3,3-trimethylbicyclo[2.2.1]heptan-2-yl 4-(dimethylamino)-4-oxobutanoate

The procedure outlined in Example 6 was repeated with N,N dimethylsuccinamic acid resulting in (2R)-1,3,3-trimethylbicyclo[2.2.1]heptan-2-yl 4-(dimethylamino)-4-oxobutanoate.

$^1$H NMR (CDCl$_3$) δ: 4.4-4.35 (d, 1H), 3.02 (s, 3H), 2.94 (s, 3H), 2.75-2.59 (m, 4H), 1.8-1.62 (m, 3H), 1.61-1.54 (d, 1H), 1.5-1.35 (m, 1H), 1.2-1.13 (d, 2H), 1.09 (s, 3H), 1.03 (s, 3H), 0.78 (s, 3H).

$^{13}$C NMR (CDCl$_3$) δ: 86.30, 48.35, 48.28, 41.36, 39.2, 29.68, 29.41, 28.1, 26.58, 25.82, 20.09, 19.36. GC-MS: 281 (M$^+$), 200, 153, 145, 128, 100, 81, 72, 55, 41, 29.

EXAMPLE 8

D-alanine fenchyl ester a) N-BOC-D-alanine fenchyl ester 0.6 g of (R)-fenchol, 0.14 g of DMAP and 1.0 g of BOC-Ala-OH were dissolved in 30 mL of dichloromethane at 0° C. 2.0 g of EDIC were added and the reaction was allowed to warm to room temperature and stirred overnight. The reaction mixture was extracted with dichloromethane versus water. The organic layer was washed with 1N HCl, NaHCO3 and brine, dried over MgSO4 and concentrated. The crude product was purified using column chromatography, to give 0.3 g of colorless oil (24%).

b) D-alanine fenchyl ester 0.3 g of N-BOC-D-alanine fenchyl ester, of Example 7, 5 mL of Dichloromethane and 5 mL of TFA were added and the mixture was stirred for 30 min at RT. The reaction mixture was diluted with 1N NaOH until pH 10 and extracted with MTBE. The organic layer was washed with 2×1N NaOH, water, dried over MgSO4 and concentrated. The crude product was purified using column chromatography, to give 0.15 g of slightly yellow oil.

$^1$H NMR (CDCl$_3$) δ: δ: 4.39 (d, 1H), 3.62-3.52 (m, 1H), 1.8-1.65 (m, 3H), 1.61-1.4 (m, 4H), 1.38-1.32 (d, 3H), 1.22-1.15 (d, 1H), 1.11 (s, 3H), 1.05 (s, 3H), 0.78 (s, 3H).

$^{13}$C NMR (CDCl$_3$) δ: 176.97, 86.60, 86.46, 50.29, 50.19, 48.38, 48.30, 41.29, 39.39, 29.69, 29.63, 26.60, 25.78, 20.97, 20.90, 20.20, 20.09, 19.33.

GC-MS: 225 (M$^+$), 137, 121, 107, 93, 81, 69, 55, 44.

EXAMPLE 9

4-oxo-4-((1R,2R,4S)-1,3,3-trimethylbicyclo[2.2.1]heptan-2-yloxy)butanoic acid 1.0 g of (R)-Fenchol was dissolved in 20 mL of Dichloromethane and cooled to 0° C., at which point 0.14 g of TMSOTf was added dropwise. The reaction was allowed to warm to room temperature and was stirred for 2 days. The reaction was quenched with MeOH, NaHCO3 solution and extracted with MTBE. The organic layer was dried over MgSO4, concentrated and purified using column chromatography, to give 0.3 g of off-white solid.

$^1$H NMR (CDCl$_3$) δ: 4.37 (d, 1H), 2.72-2.67 (m, 4H), 1.78-1.64 (m, 3H), 1.62-1.54 (m, 1), 1.52-1.39 (m, 1H), 1.22-1.16 (m, 1H), 1.12-1.08 (m, 1H), 1.09 (s, 3H), 1.03 (s, 3H), 0.77 (s, 3H)

$^{13}$C NMR (CDCl$_3$) δ: 178.16, 172.38, 86.78, 48.33, 48.27, 41.35, 39.43, 29.65, 29.09, 29.05, 26.58, 25.78, 20.02, 19.27

GC-MS: 254 (M$^+$), 175, 154, 121, 111, 101, 93, 81, 69, 55, 41.

EXAMPLE 10

Cooling Intensity

A small group of panelists was asked to taste various aqueous solutions of compounds of formula (I) and indicate which solutions had a cooling intensity similar to or slightly higher than that of a solution of menthol at 2 ppm. The results are shown in Table 1.

TABLE 1

| Chemical | Example | Concentration | Odor |
|---|---|---|---|
| Comparison: l-Menthol | | 2.0 ppm | Minty |
| Comparison: N-ethyl p-menthanecarboxamide (WS-3) | | 1.5 ppm | None |
| 4-oxo-4-((1S,2R,4S)-1,7,7-trimethylbicyclo[2.2.1]heptan-2-yloxy)butanoic acid | 1 | 0.003 ppm | None |
| 4-oxo-4-((1R,2R,4R)-1,7,7-trimethylbicyclo[2.2.1]heptan-2-yloxy)butanoic acid | 4 | 0.001 ppm | None |
| Ethyl (2R)-1,3,3-trimethylbicyclo[2.2.1]heptan-2-yl malonate | 6 | 0.10 ppm | None |
| (2R)-1,3,3-trimethylbicyclo[2.2.1]heptan-2-yl 4-(dimethylamino)-4-oxobutanoate | 7 | 0.002 ppm | None |
| D-alanine fenchyl ester | 8 | 0.20 ppm | None |
| 4-oxo-4-((1R,2R,4S)-1,3,3-trimethylbicyclo[2.2.1]heptan-2-yloxy)butanoic acid | 9 | 0.10 ppm | None |

As can be seen from the resells above, the subject compounds are at least 10 times stronger than 1-menthol and also stronger than WS-3.

EXAMPLE 11

Application in Toothpaste a) Control, Peppermint Oil

| Opaque toothgel | 99.20 g |
|---|---|
| Peppermint oil, terpeneless | 0.50 g |
| Saccharin | 0.30 g |

The materials were mixed in the toothgel, a piece of toothgel was put on a toothbrush and a panelist's teeth were brushed. The mouth was rinsed with water and the water spat out. An intense cooling sensation was felt by the panelist in all areas of the mouth. The cooling perception lasted for 40 minutes.

b) 4-((1S,2S,4R)-bicyclo[2.2.1]heptan-2-yloxy)-4-oxobutanoic acid

| Opaque toothgel | 99.20 g |
|---|---|
| Compound of example 3 as a 1% solution Peppermint oil, terpeneless | 0.10 g |
| Peppermint oil, terpeneless | 0.40 g |
| Saccharin | 0.30 g |

The materials were mixed in the toothgel, a piece of toothgel was put on a toothbrush and a panelist's teeth were brushed. The mouth was rinsed with water and the water spat out. An intense cooling sensation was felt by the panelist in all areas of the mouth. The cooling perception was rated 24% higher than the control and lasted for 70 minutes.

c) Ethyl (2R)-1,3,3-trimethylbicyclo[2.2.1]heptan-2-yl malonate

| Opaque toothgel | 99.20 g |
|---|---|
| Compound of example 6 as a 1% solution Peppermint oil, terpeneless | 0.10 g |
| Peppermint oil, terpeneless | 0.40 g |
| Saccharin | 0.30 g |

The materials were mixed in the toothgel, a piece of toothgel was put on a toothbrush and a panelist's teeth were brushed. The mouth was rinsed with water and the water spat out. An intense cooling sensation was felt by the panelist in all areas of the mouth. The cooling perception was rated 18% higher than the control and lasted for 60 minutes.

d) Ethyl (2R)-1,3,3-trimethylbicyclo[2.2.1]heptan-2-yl malonate

| Opaque toothgel | 99.20 g |
|---|---|
| Compound of example 6 as a 1% solution Peppermint oil, terpeneless | 0.50 g |
| Saccharin | 0.30 g |

The materials were mixed in the toothgel, a piece of toothgel was put on a toothbrush and a panelist's teeth were brushed. The mouth was rinsed with water and the water spat out. An intense cooling sensation was felt by the panelist in all areas of the mouth. The cooling perception was rated 95% higher than the control and lasted for 65 minutes.

e) 4-oxo-4-((1R,2R,4R)-1,7,7-trimethylbicyclo[2.2.1]heptan-2-yloxy)butanoic acid

| Opaque toothgel | 99.20 g |
|---|---|
| Compound of example 4 as a 1% solution Peppermint oil, terpeneless | 0.05 g |
| Peppermint oil, terpeneless | 0.45 g |
| Saccharin | 0.30 g |

The materials were mixed in the toothgel, a piece of toothgel was put on a toothbrush and a panelist's teeth were brushed. The mouth was rinsed with water and the water spat out. An intense cooling sensation was felt by the panelist in all areas of the mouth. The cooling perception was rated 100% higher than the control and lasted for 40 minutes.

f) D-alanine fenchyl ester

| Opaque toothgel | 99.20 g |
|---|---|
| Compound of example 8 | 0.025 g |
| Peppermint oil, terpeneless | 0.50 g |
| Saccharin | 0.30 g |

The materials were mixed in the toothgel, a piece of toothgel was put on a toothbrush and a panelist's teeth were brushed. The mouth was rinsed with water and the water spat out. An intense cooling sensation was felt by the panelist in all areas of the mouth. The cooling perception was rated 30% higher than the control and lasted for over 35 minutes.

EXAMPLE 12

Application in Chewing Gum a) Control, Peppermint Oil

| | |
|---|---|
| Gum Base Solsona-T | 30 g |
| Sorbital powdered | 50.6 g |
| Maltitol Syrup 85% | 9 g |
| Mannitol powdered | 5 g |
| Glycerin | 5 g |
| Acesulfame potassium (Ace-K ™) | 0.09 g |
| Aspartame | 0.21 g |
| Peppermint oil, terpeneless | 0.50 g |

The gum base, and half of the sorbitol were mixed, maltitol syrup was added and then mixed with the gum mass. The rest of the powdered ingredients (rest of the sorbitol, mannitol, ace-K, aspartame) were added and mixed for about 1 minute, at which point glycerine was added and the gum mass was mixed for about 5 minutes, to form the blank chewing gum mass. Peppermint oil was worked into the mass and a piece of the resulting gum (2 g) was chewed by a panelist for 20 mm and spat out. A cooling sensation was felt by the panelist in all areas of the mouth. The cooling perception lasted far 50 minutes.

b) 4-((1S,2S,4R)-bicyclo[2.2.1]heptan-2-yloxy)-4-oxobutanoic acid

Compound of example 3 as a 1% solution Peppermint oil, terpeneless 0.50 g

The chemical in the peppermint oil was worked into the blank chewing gum mass from Example 12 a) and a piece of the resulting gum (2 g) was chewed by a panelist for 20 minutes and spat out. A cooling sensation was felt by the panelist in all areas of the mouth. The cooling perception was rated 43% higher than the control and lasted for over 60 minutes.

c) 4-oxo-4-((1R,2R,4R)-1,7,7-trimethylbicyclo[2.2.1]heptan-2-yloxy)butanoic acid

| | |
|---|---|
| Compound of example 4 as a 1% solution Peppermint oil, terpeneless | 0.05 g |
| Peppermint oil, terpeneless | 0.45 g |

The chemical and peppermint oil was worked into the blank chewing gum mass from Example 12 a) and a piece of the resulting gum (2 g) was chewed by a panelist for 20 minutes and spat out. A cooling sensation was felt by the panelist in all areas of the mouth. The cooling perception was rated 40% higher than the control and lasts for over 60 minutes.

d) Ethyl (2R)-1,3,3-trimethylbicyclo[2.2.1]heptan-2-yl malonate

Compound of example 6 as a 1% solution Peppermint oil, terpeneless 0.50 g

The chemical in the peppermint oil was worked into the blank chewing gum mass from Example 12 a) and a piece of the resulting gum (2 g) was chewed by a panelist for 20 minutes and spat out. A cooling sensation was felt by the panelist in all areas of the month. The cooling perception was rated 27% higher than the control and lasted for over 60 minutes.

Although the compositions, products and methods have been described in detail through the above detailed description and the preceding examples, these examples are for the purpose of illustration only and it is understood that variations and modifications can be made by one skilled in the art without departing from the spirit and the scope of the invention. It should be understood that the embodiments described above are not only in the alternative, but can be combined.

We claim:

1. A cooling composition adapted to be applied to skin or mucous membranes comprising a composition base and (2R)-1,3,3-trimethylbicyclo[2.2.1]heptan-2-yl 4-(dimethylamino)-4-oxobutanoate.

2. A composition according to claim 1, which additionally comprises at least one known cooling compound.

3. A composition according to claim 2, in which the known cooling compound is at least one selected from the group consisting of menthol, menthone, isopulegol, N-ethyl p-menthanecarboxamide (WS-3), N,2,3-trimethyl-2-isopropylbutanamide (WS-23), ethyl N[[5-methyl-2-(isopropyl)cyclohexyl]carbonyl]glycinate, menthyl lactate, menthone glycerine acetal, mono-menthyl succinate, mono-monomenthyl glutarate, O-menthyl glycerine and 2-sec-butylcyclohexanone, menthane, camphor, pulegol, cineol, mint oil, peppermint oil spearmint oil, eucalyptus oil, 3-1-menthoxypropane-1,2-diol, 3-1-menthoxy-2-methylpropane-1,2-diol, p-menthane-3,8-diol, 2-1-menthoxyethane-1-ol, 3-1-menthoxypropane-1-ol, and 4-1-menthoxybutane-1-ol.

4. A product selected from at least one of products that are applied to the mucous membranes, products that are applied to the oral mucosa, and products that are applied to the skin, comprising a product base and an effective amount of cooling compound (2R)-1,3,3-trimethylbicyclo[2.2.1]heptan-2-yl 4-(dimethylamino)-4-oxobutanoate.

5. The product according to claim 4, wherein the products that are applied to the skin comprise at least one of perfumes, toiletries, lotions, oils, skin-care cosmetics, cleansing tissues, talcum powders, lotions, tonics, lotions, creams, salve, balms, gels, sprays, sunburn cosmetics, soaps, toothpicks, lipsticks, bathing agents, deodorants, or antiperspirants.

6. The product according to claim 4, wherein the products that are applied to the mucous membranes or oral mucosa comprise at least one of dentifrices, toothpastes, mouthwashes, throat sprays, medicines, tablets, foodstuffs, beverages, confectionery, nasal care products, tobacco products, oral care products, ingestible products or chewing gums; optionally wherein the foodstuffs or beverages comprise at least one of alcoholic beverages, non-alcoholic beverages, fruit juice beverages, fruit liquors, milk drinks, carbonated beverages, refreshing beverages, health drinks, nutrient drinks, instant beverages, frozen confectioneries, ice creams, sorbets, desserts, jelly, pudding, confectioneries, cakes, cookies, chocolates, jams, candies, breads, tea beverages, green tea, black tea, chamomile tea, mulberry leaf tea, Roobos tea, peppermint tea, soups, seasonings, or snack foods.

7. (2R)-1,3,3-trimethylbicyclo[2.2.1]heptan-2-yl 4-(dimethylamino)-4-oxobutanoate.

* * * * *